United States Patent [19]
Lifton et al.

[11] Patent Number: 5,529,900
[45] Date of Patent: Jun. 25, 1996

[54] DIRECT GENETIC TEST FOR GLUCOCORTICOID-REMEDIABLE ALDOSTERONISM

[75] Inventors: Richard P. Lifton; Jean-Marc Lalouel, both of Salt Lake City, Utah

[73] Assignees: Brigham and Women's Hospital, Boston, Mass.; University of Utah, Salt Lake City, Utah

[21] Appl. No.: 2,323

[22] Filed: Jan. 8, 1993

[51] Int. Cl.$^6$ ............................ C12Q 1/68; C12P 19/34
[52] U.S. Cl. ................................................ 435/6; 435/91.2
[58] Field of Search .................... 435/6, 91.2; 935/77, 935/78

[56] References Cited

PUBLICATIONS

Ulick, S., et al., "Biosynthesis of 18–Oxocortisol by Aldosterone–producing Adrenal Tissue," *The Journal of Biological Chemistry* 258(9):5498–5502 (1983).

Chu, M. D., et al., "Isolation and Identification of 18–Hydroxycortisol from the Urine of Patients with Primary Aldosteronism," *The Journal of Biological Chemistry* 257(5):2218–2224 (1982).

Ogishima, T., et al., "Aldosterone Synthase Cytochrome P–450 Expressed in the Adrenals of Patients with Primary Aldosteronism," *The Journal of Biological Chemistry* 266(18):10731–10734 (1991).

White, P. C., et al., "Characterization of frequent deletions causing steroid 21–hydroxylase deficiency," *Proc. Natl. Acad. Sci. USA* 85:4436–4440 (1988).

Chua, S. C., et al., "Cloning of cDNA encoding steroid 11β–hydroxylase (P450c11)," *Proc. Natl. Acad. Sci. USA* 84:7193–7197 (1987).

Gomez–Sanchez, C. E., et al., "Elevated Urinary Excretion of 18–Oxocortisol in Glucocorticoid–Suppressible Aldosteronism," *Journal of Clinical Endocrinology and Metabolism* 59:1022–1024 (1984).

Ulick, S., et al., "Defective Fasciculata Zone Function as the Mechanism of Glucocorticoid–Remediable Aldosteronism," *Journal of Clinical Endocrinology and Metabolism* 71(5):1151–1157 (1990).

Ulick, S., et al., "Measurement of 4 Urinary C–18 Oxygenated Corticosteroids by Stable Isotope Dilution Mass Fragmentography," *J. Steroid Biochem. Molec. Biol.* 38(1):59–66 (1991).

Curnow, K. M., et al., "The Product of the CYP11B2 Gene is Required for Aldosterone Biosynthesis in the Human Adrenal Cortex," *Mol. Endo.* 5(10):1513–1522 (1991).

Pascoe, L., et al., "Glucocorticoid–suppressible hyperaldosteronism results from hybrid genes created by unequal crossovers between CYP11B1 and CYP11B2," *Proc. Natl. Acad. Sci. USA* 89:8327–8331 (1992).

Ganguly, A., "Glucocorticoid–Suppressible Hyperaldosteronism: An Update," *Am. Jour. of Med.* 88:321–324 (1990).

Lifton, R. P. et al., "A chimaeric 11 β–hydroxylase/aldosterone synthase gene causes glucocorticoid–rememdiable aldosteronism and human hypertension," *Nature*, 355:262–265 (1992).

Lifton, R. P. et al., "Hereditary hypertension caused by chimaeric gene duplications and ectopic expression of aldosterone synthase," *Nature Genetics*, 2:66–74 (1992).

*Primary Examiner*—W. Gary Jones
*Assistant Examiner*—Eggerton Campbell
*Attorney, Agent, or Firm*—Hamilton, Brook, Smith & Reynolds

[57] ABSTRACT

A method of screening for glucocorticoid remediable aldosteronism (GRA) in a mammal by detecting the presence or absence of a chimaeric gene duplication resulting from unequal crossing over of the 11, β-hydroxylase and aldosterone synthase genes, or the product encoded by the chimaeric gene duplication. Presence of the chimaeric gene duplication or its encoded product is indicative of a mammal afflicted with GRA and absence of the chimaeric gene duplication or its product is indicative of a mammal not afflicted with GRA.

8 Claims, 6 Drawing Sheets

DIRECT GENETIC TEST FOR GLUCOCORTICOID-REMEDIABLE ALDOSTERONISM

FUNDING

Work described herein was funded by the National Institute of Health Research Grant No. 5R01 HL45325-02. The government has certain rights herein.

BACKGROUND OF THE INVENTION

Hypertension, a widespread disorder of unknown cause, is responsible for over 200,000 deaths in the United States alone each year due to heart attack, stroke, and end stage renal disease. Population-based epidemiologic studies, adoption studies and twin studies have demonstrated a strong genetic component to hypertension.

Glucocorticoid-remediable aldosteronism (GRA) is a disorder responsible for a form of hypertension. This disease is characterized by variably elevated levels of aldosterone, an adrenal gland steroid which regulates sodium-potassium metabolism, and high levels of the abnormal adrenal steroids, 18-hydroxycortisol and 18-oxocortisol.

Currently the two ways to diagnose GRA require either measurement of aldosterone levels before and after administration of a glucocorticoid drug (e.g. dexamethasone), or measurement of 18-oxocortisol, 18-hydroxycortisol and the ratio of 18-oxocortisol to tetrahydroaldosterone in a 24 hour urine collection. Both of these tests are cumbersome and expensive and the latter test is available in the United States in only a few laboratories.

Due to the difficulties associated with diagnosis of GRA, it is most probably an underdiagnosed disease. A simple, widely available test for GRA would facilitate early diagnosis and treatment for those afflicted with GRA which would be extremely beneficial since the hypertension associated with the disease is often severe, dating from early childhood.

SUMMARY OF THE INVENTION

This invention relates to a method of screening directly for glucocorticoid remediable aldosteronism (GRA) with high sensitivity and specificity. The method is based upon Applicant's discovery that GRA is caused by a chimaeric gene duplication arising from unequal crossing over between the steroid 11β-hydroxylase gene (11-OHase) and the aldosterone synthase gene (AldoS), each of which normally encode different enzymes involved in steroid biosynthesis. As used herein, the terms "crossing over" refers to the reciprocal exchange of material between chromosomes at identical sites on the chromosomes during genetic recombination; "unequal crossing over" refers to reciprocal exchange of material between chromosomes at nonidentical sites on the chromosomes during genetic recombination due to misalignment of the chromosomes. The product expressed by this chimaeric gene duplication accounts for the known biochemistry, physiology, and genetics of GRA.

The discovery of the genetic cause of GRA allows for the use of a direct screening test which detects the presence or absence of this chimaeric gene duplication or the product encoded by the chimaeric gene duplication in the mammal using any sample from the mammal containing the chimaeric gene duplication or its encoded product. Presence of the chimaeric gene or the expressed product indicates a mammal afflicted with GRA and absence of the chimaeric gene or its expressed product indicates a mammal not afflicted with GRA.

This invention overcomes the problems of previous tests for the disorder which require either investigation of patients before and after pharmacological intervention or measurement of abnormal steroids in urine collections; these latter measurements are not widely available. Methods of detection of the present invention include electrophoretic techniques, recombinant DNA techniques, or antibody-mediated techniques. Of most importance, methods of detection used by this invention are standard tools of molecular biology and are available in most laboratories.

The degree of specificity and sensitivity of this test has been remarkable. The results indicate 100% sensitivity and 100% specificity of chimaeric 11-OHase/AldoS gene duplications for GRA.

The method of the present invention can be applied to all hypertensive subjects, or can be applied to more selective hypertensive subjects, such as patients with pediatric hypertension, hypertensives with signs of aldosteronism who do not have aldosterone secreting tumors, or hypertensives who have suppressed plasma renin activity. In addition, identification of the disease motivates screening of relatives of hypertensives with strong family histories of hypertension, since GRA is an autosomal dominant disorder and 50% of a patients' first-degree relatives will, on average, also have the disease.

This test is clinically relevant since correct diagnosis of GRA indicates specific therapy. None of the standard therapies for GRA, that is, exogenous glucocorticoids, blockade of the aldosterone receptor, or inhibition of the sodium channel activated by aldosterone, is commonly offered to hypertensive patients, further underscoring the importance of making the diagnosis of GRA.

Perhaps most important is that Applicant's discovery allows for improved treatment of GRA. Interference with expression of the chimaeric gene duplication or its encoded product, or interference with the action of the resulting hormones, can inhibit onset or progression of the disease. Given the often severe hypertension in GRA with attendant early morbidity and mortality and poor response to conventional therapy, the expected benefit from early diagnosis and improved treatment of cases is high.

DETAILED DESCRIPTION OF THE INVENTION

Glucocorticoid-remediable aldosteronism (GRA) is characterized by autosomal dominant transmission of hypertension with excessive secretion of aldosterone and by high levels of the abnormal adrenal steroids 18-oxocortisol and 18-hydroxycortisol, which are all under control of adrenocorticotropic hormone (ACTH) and suppressible by glucocorticoids, which are hormones that help adapt to stress. Applicant has shown GRA cosegregates with a chimaeric gene duplication arising from an unequal crossing over between steroid 11β-hydroxylase (11-OHase) and aldosterone synthase (AldoS) genes. In the normal adrenal gland, AldoS activity is present only in the adrenal glomerulosa where it catalyzes the final two steps in aldosterone biosynthesis. Aldosterone is produced in the glomerulosa under regulation of angiotensin II, a potent vasopressor. Steroid 11-OHase is normally expressed in the adrenal fasciculata where it is involved in the biosynthesis of cortisol and in the adrenal glomerulosa where it is involved in the biosynthesis of aldosterone. In the fasciculata, 11-OHase is regulated by ACTH.

In the GRA adrenal gland, the chimaeric gene is expressed in the adrenal fasciculata under control of ACTH by virtue of the 5' regulatory coding sequence of 11-OHase, but has AldoS enzymatic activity due to coding sequence of the AldoS gene. Expression of the chimaeric gene results in ectopic activity of the gene product in the adrenal fasciculata causing metabolism of cortisol to 18-hydroxycortisol and 18-oxocortisol, as well as production of aldosterone. This dysregulation of aldosterone secretion results in an excess of aldosterone and consequent hypertension. Thus, in an individual afflicted with GRA, the aldosterone produced in the adrenal fasciculata is under control of ACTH and can consequently be suppressed by exogenous glucocorticoids, which is a current treatment of GRA.

Figure 2:
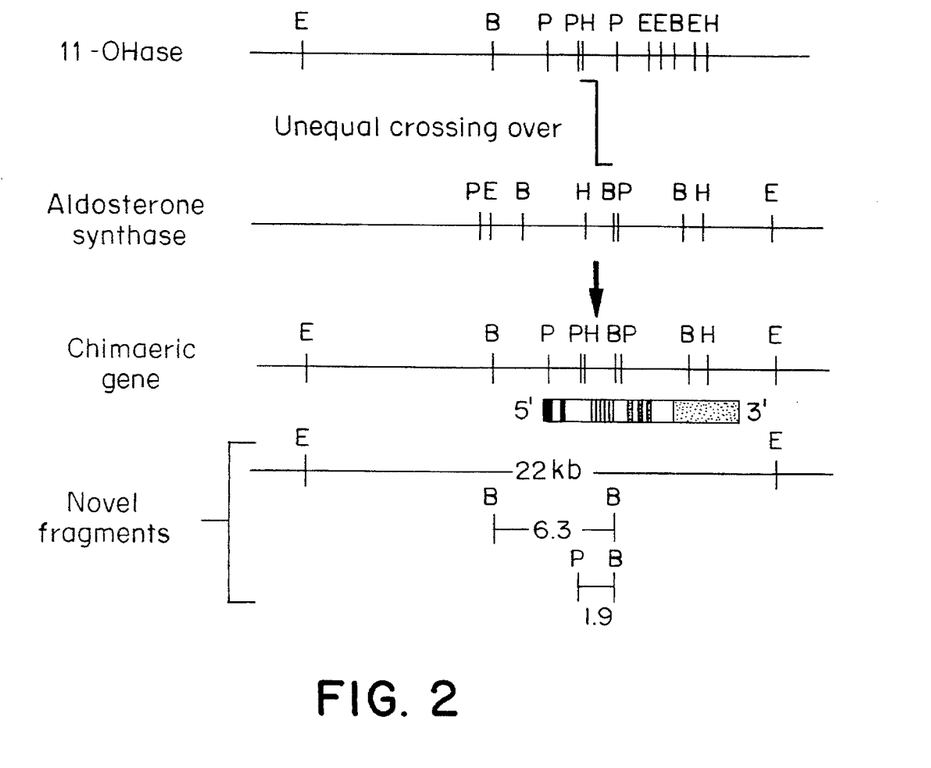
FIG. 2 is a schematic representation of the location of cleavage sites for restriction enzymes in 11-OHase, AldoS, and the chimaeric gene. Sites cut by restriction enzymes BamHI (B), EcoRI (E), HindIII (H), and PvuII (P) are shown and the location of the exons of the chimaeric gene on the restriction enzyme map are indicated.

The genes encoding steroid 11-OHase and AldoS are 95% identical in nucleotide sequence and are both present on chromosome 8. Fragmenting the genomic DNA of normal individuals with restriction enzymes produces two fragments representing the 11-OHase and AldoS genes upon hybridization with appropriate probes. Use of certain restriction enzymes to fragment the genomic DNA of GRA afflicted individuals reveals a novel DNA fragment upon hybridization with appropriate probes in addition to the two fragments representing 11-OHase and AldoS. This novel fragment represents the chimaeric gene duplication associated with GRA and as shown in FIG. 2 and demonstrated in Example 1, the size of the novel fragment depends on the restriction enzyme used.

Figure 1:
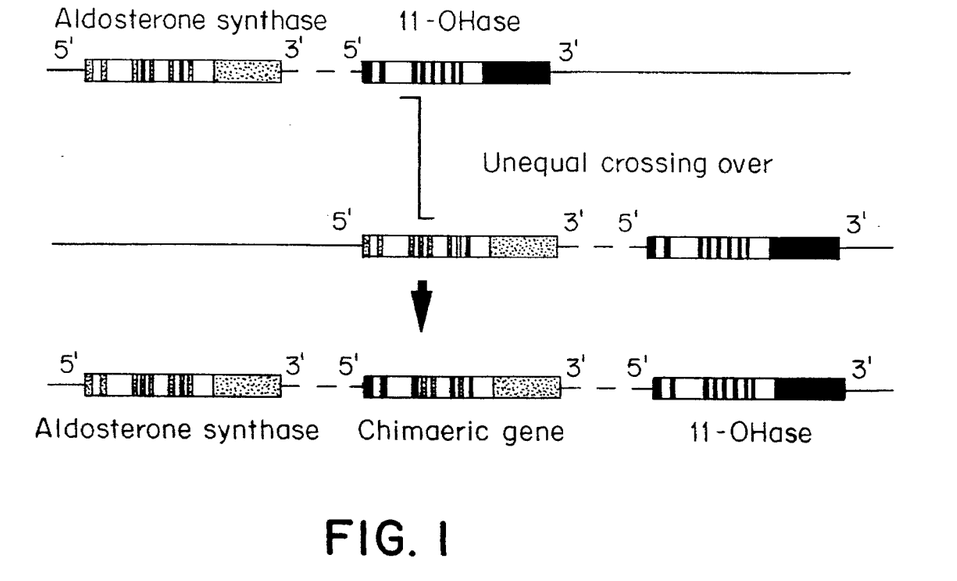
FIG. 1 is a schematic representation depicting unequal crossing over between 11β-hydroxylase (11-OHase) and aldosterone synthase (AldoS). Each gene is represented by a wide bar, with the location of exons indicated by either black (11-OHase) or stippled bands (AldoS). In this example, unequal crossing over is depicted as occurring in the intron (white spaces) between exons 3 and 4.

The gene duplication associated with GRA is a chimaeric 5' 11-OHase/3'AldoS gene as demonstrated in Examples 2 and 3. This indicates an origin from unequal crossing over upstream of intron 5 in both the 11-OHase and AldoS gene as shown in FIG. 1. Additional support for the structure of the chimaeric gene is Applicants' identification of cross over breakpoints which would result in the chimaeric gene duplication as shown in Example 4, and evidence for physical and genetic linkage of the normal 11-OHase and AldoS genes as shown by pulse-field gel electrophoresis in Example 5, and genetic linkage analysis which is the tendency of genes to be inherited together as a result of their close proximity on the same chromosome.

The discovery of the genetic cause of GRA provides a method for a direct test for the disease with 100% sensitivity and specificity. The chimaeric gene duplication is carried by all 29 patients with GRA from 12 pedigrees, while 407 individuals not known to have a diagnosis of GRA did not display the anomalous chimaeric gene duplication associated with GRA.

The method of the present invention can be used to detect either the chimaeric gene duplication or its gene product in a mammal. Any sample from a mammal which will yield a nucleic acid sequence representative of a mammal's genome or the product encoded by the nucleic acid sequence can be used to screen for GRA. Such samples include but are not limited to any body fluid such as blood, lymph, urine or spinal fluid, or tissue such as organ tissue. An example of extraction of genomic DNA from peripheral venous blood used to detect the chimaeric gene duplication is provided in Example 1.

Analysis of the sample obtained from the mammal for the presence of the chimaeric gene can be performed using methods involving detection of nucleic acids. For example, as described in Example 1, a Southern blot analysis of genomic DNA of test individuals was performed on genomic DNA extracted from peripheral blood. The genomic DNA is digested with a restriction enzyme, such as BamHI, which recognizes short specific sequences of DNA and cleaves the DNA at those points, producing fragments of DNA. These DNA fragments are separated by gel electrophoresis and transferred to a nylon membrane containing labeled DNA sequences complementary to the 11-OHase or AldoS gene. BamHI digested genomic DNA produces an 8.5 kb fragment from the 11-OHase gene and a 4.5 kb fragment from the AldoS gene in normal and GRA afflicted mammals which bind, or hybridize, to the DNA fragments on the nylon membrane containing sequences complementary to these genes. In addition, BamHI digested DNA of individuals afflicted with GRA will have a 6.3 kb fragment from the chimaeric gene which also binds to the complementary DNA sequences on the nylon membrane. The location of these complementary sequences hybridized to the genomic DNA can be detected by several means including, but not limited to, radioactivity or fluorescence. Such a method makes the use of control DNA samples feasible, in which one control DNA sample is negative for GRA and another control DNA sample is positive for GRA. The result produced by the DNA of the individual being tested for GRA is compared to the results produced by the negative and positive DNA control samples which are analyzed along with the DNA of the individual being tested for GRA. If the result produced by the DNA of the individual being tested for GRA is similar to the result produced by the negative DNA control, then the individual is not afflicted with GRA; if the result produced by the individual being tested for GRA is similar to the result produced by the positive DNA control, then the individual is afflicted with GRA.

Other restriction enzymes can be used to fragment the genomic DNA similarly to produce the characteristic fragments found in normal and GRA afflicted individuals in addition to the abnormal fragment(s) found in GRA afflicted individuals. An example of another appropriate restriction enzyme is EcoRI which produces a 16.3 kb fragment from the 11-OHase gene and a 13.1 kb fragment from the AldoS gene in normal and GRA afflicted individuals. An additional 22.3 kb fragment is produced in GRA afflicted individuals. Also, the restriction enzyme ClaI produces a 130 kb fragment containing the 11-OHase and AldoS gene in normal and GRA afflicted individuals and an additional 180 kb fragment in GRA afflicted individuals.

Those skilled in the art will recognize or be able to determine using no more than routine experimentation, other suitable conditions for detecting GRA by the Southern hybridization technique. In principle, many different restriction enzymes (functioning alone or in combination with other restriction enzymes), probes specific for the genes associated with GRA and hybridization techniques are available to perform Southern hybridization.

Detection of the chimaeric gene duplication can also be achieved using polymerase chain reaction (PCR) technology. Specifically, the chimaeric gene duplications can be detected by design and use of one primer specific for the 11-hydroxylase gene sequences and another primer specific for the aldosterone synthase gene sequences such that only chimaeric genes containing both 11-hydroxylase and aldosterone synthase gene sequences can yield products of the proper length in PCR. Alternatively, the single strand conformational polymorphism method detects base changes in a given sequence of genomic DNA using PCR. Specific regions of genomic sequences can be labeled and amplified simultaneously using labeled substrates in the polymerase chain reaction. Subsequent analysis of these selected sequences amplified by PCR in a nondenaturing gel system reveals that the electrophoretic mobility of single-stranded nucleic acid varies according to its size and sequence. Orita, M., et al., *Genomics,* 5:874-879 (1989). Thus, a change in the nucleic acid sequence will be reflected in the nondenaturing gels. This technique can also be used to detect the ratio of alleles of genes such as AldoS which varies in GRA afflicted individuals as is illustrated in Example 2.

Other modes of nucleic acid detection can be used for this method. For instance, a denaturing gradient gel electrophoresis technique takes advantage of the fact that the mobility of partially melted DNA is virtually zero in polyacrylamide gel electrophoresis and that the site of a mismatch tends to melt early. Myers, R. M., et al., *Nature,* 313:495-498 (1985).

Other methods of nucleic acid detection methods include oligonucleotide hybridization (Conner, B. J., et al., *Proc. Natl. Acad. Sci. USA,* 80:278-282 (1983) ligase-mediated gene detection (Landegren, U., et al., *Science,* 241:1077-1080 (1988) and RNaseH digestion techniques (Winter, E., et al., *Proc. Natl. Acad. Sci. USA,* 82:7575-7579 (1985) .

Alternatively, the sample obtained from the mammal can be analyzed for the presence of the protein product expressed by the chimaeric gene duplication associated with GRA using a variety of methods. Such methods include electrophoretic assays, enzymatic assays, colorimetric assays, fluorescent assays, or chromatographic assays.

Those skilled in the art will recognize, or be able to determine using no more than routine experimentation, other suitable techniques to detect the chimaeric gene duplication or its encoded product associated with GRA.

A method of screening for GRA via a genetic test will have many applications, which include but are not limited to the following.

One area of application is the rapid, simple screening of GRA in a mammal. Combining this invention with polymerase chain reaction (PCR) technology will permit batch screening of a large number of samples for GRA. Also, a direct test for GRA can be used as a research tool in order to determine the prevalence of GRA in the hypertensive population. While GRA is thought to be a rare disease, no systematic studies have been performed, and there is reason to suspect the disease is underdiagnosed. The invention can also be used as a clinical tool in patients in whom the likelihood of GRA is increased. The spectrum of patients in whom similar mutations might be found has not been defined. The diagnosis should be considered in patients with strong family histories of early onset of hypertension, particularly if signs of aldosteronism are present. In addition, individuals who are at-risk relatives of GRA patients are candidates for screening.

This invention also has significant application in aspects of GRA treatment. Knowing the location of the chimaeric gene duplication allows treatment of GRA using gene therapy techniques, such as antisense technology, which can target the specific chimaeric gene and block its activation or expression. Also treatment of GRA can be aimed at the gene product where its expression can be prevented or its activity inhibited once the product is expressed using techniques such as antibody mediated treatment. Therefore, onset or progression of GRA can be prevented using the method of the present invention.

Those skilled in the art will recognize, or be able to determine using no more than routine experimentation, other suitable therapeutic techniques to treat GRA using the present method.

The invention is further and more specifically illustrated by the following examples.

EXAMPLE 1

DIGESTION OF GENOMIC DNA OF INDIVIDUALS AFFLICTED WITH GRA WITH RESTRICTION ENZYMES YIELDS CHARACTERISTIC SIGNATURES OF CHIMAERIC GENE DUPLICATIONS UPON HYBRIDIZATION WITH APPROPRIATE PROBES

Total genomic DNA was extracted from 10-20 ml of peripheral venous blood as described in the following literature reference, the teachings of which are incorporated by reference: Bell,G., Karam,J. and Rutter, W., "Polymorphic DNA region adjacent to the 5' end of the human insulin gene" *Proc Natl Acad Sci USA* 78:5759-5763 (1981).

The probes were prepared in the following manner. A segment spanning exon 3-4 of the 11-OHase gene was prepared by PCR using specific primers and cosmid c110H26 as a template. The resulting fragment was purified on an agarose gel, and labeled with $\alpha$-$^{32}$P dCTP by random priming. A probe specific for the flanking region of 11-OHase was labelled by PCR using specific primers 11OH-51 and 11OH-54 and cosmid c110H26 as a template. This probe is 225 bp in length and covers 140-365 bp upstream of exon 1. Labeled probes were denatured and hybridized to filters as described in the following literature reference, the teachings of which are incorporated by reference: Lifton, R. P., Sardet, C., Pouyssegur, J. and Lalouel J-M, "Cloning of the human genomic amiloride-sensitive Na+/H+ antiporter gene, identification of genetic polymorphisms, and localization on the genetic map of chromosome 1p" *Genomics,* 7:131-135 (1990).

The genomic DNA was then analyzed by Southern blot analysis. Genomic DNA was digested with either the restriction enzyme BamHI or EcoRI, fractionated via agarose gel electrophoresis (0.5% agarose gel for EcoRI blots, 0.7% agarose blots for BamHI blots), transferred to nylon membranes (Hybond-N+, Amersham) after depurination with 2 washes for 5 minutes in 0.25 M HCL, followed by denaturation in 0.4 M NaOH for 15 minutes, and hybridized with the exon 3-4 probe from 11-OHase.

Figure 3:
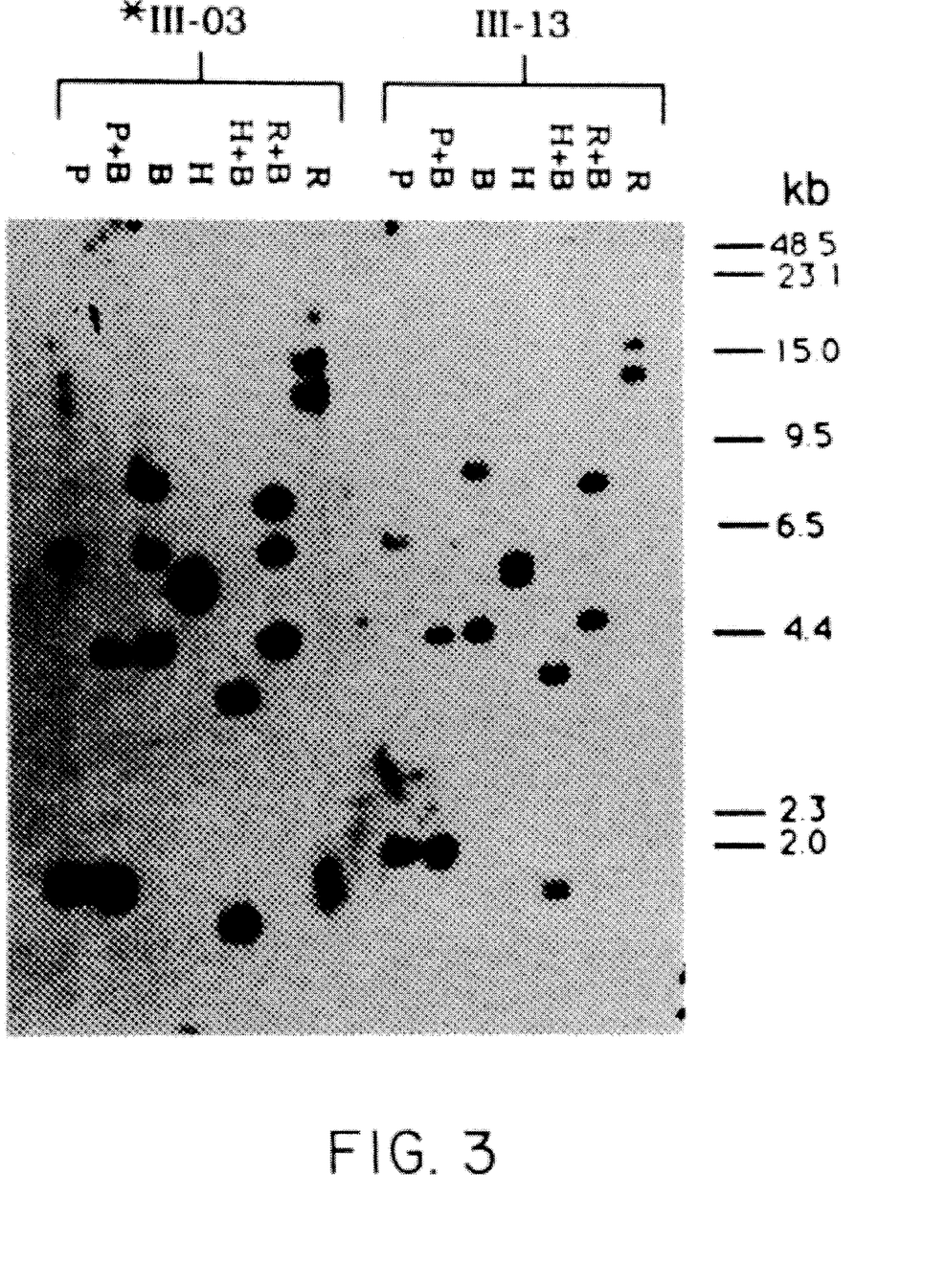
FIG. 3 is a photograph of a gel depicting hybridization of exon 3-4 probe to genomic DNA of an affected (*III-03) and unaffected (III-13) subject digested with the various restriction enzymes PvuII (P), BamHI (B), HindIII (H) and EcoRI (R) singly and in combination.

Subjects with GRA all have both the 6.3 kb BamHI fragment and the 22 kb EcoRI fragment characteristic of the gene duplication arising via unequal crossing over between 11-OHase and AldoS genes upstream of intron 5. The products of BamHI digestion can detect chimaeric genes arising from unequal crossing over anywhere between the 5' end of the genes up to intron 5; EcoRI digestion can detect chimaeric genes arising from unequal crossing over anywhere between the 5' end of the genes and intron 8. Importantly, the size of the resulting fragments from the duplicated gene will always be 6.3 kb (BamHI) and 22 kb (EcoRI), regardless of the exact site of crossing over within these intervals. See FIG. 3.

EXAMPLE 2

AMPLIFICATION OF MARKER AldoX9 SHOWING DUPLICATION OF EXON 9 OF AldoS PROVIDING FURTHER EVIDENCE FOR THE 5' 11-Hase/3' AldoS CHIMAERIC GENE DUPLICATION ASSOCIATED WITH GRA Further evidence supporting gene duplication comes from quantitation of PCR products in pedigree members heterozygous for the single strand conformational polymorphism (SSCP) marker AldoX9, which specifically amplifies a segment of exon 9 of AldoS. If unequal crossing over has resulted in a gene duplication of the structure shown, the 3' end of the AldoS including exon 9 should be duplicated and therefore present three times per diploid genome; consequently, heterozygotes for polymorphic markers at the 3' end of this gene should show a 2:1 ratio of intensity of alleles.

Polymerase chain reaction (PCR)-based markers were genotyped by amplification of genomic DNA in the presence of $^{32}$P-labeled dTCP; unless specified, the PCR was for 30 cycles of 94° C. for 45 seconds, 60° C. for 45 seconds, 72° C. for 45 seconds. Products were analyzed by single-stranded conformational polymorphism as described in the following literature reference, the teachings of which are incorporated by reference: Orita, M., Suzuki, Y., Sekiya, T. and Hayashi, K., "Rapid and sensitive detection of point mutations and DNA polymorphisms using the polymerase chain reaction", *Genomics*, 5:874–879 (1989).

Figure 4:
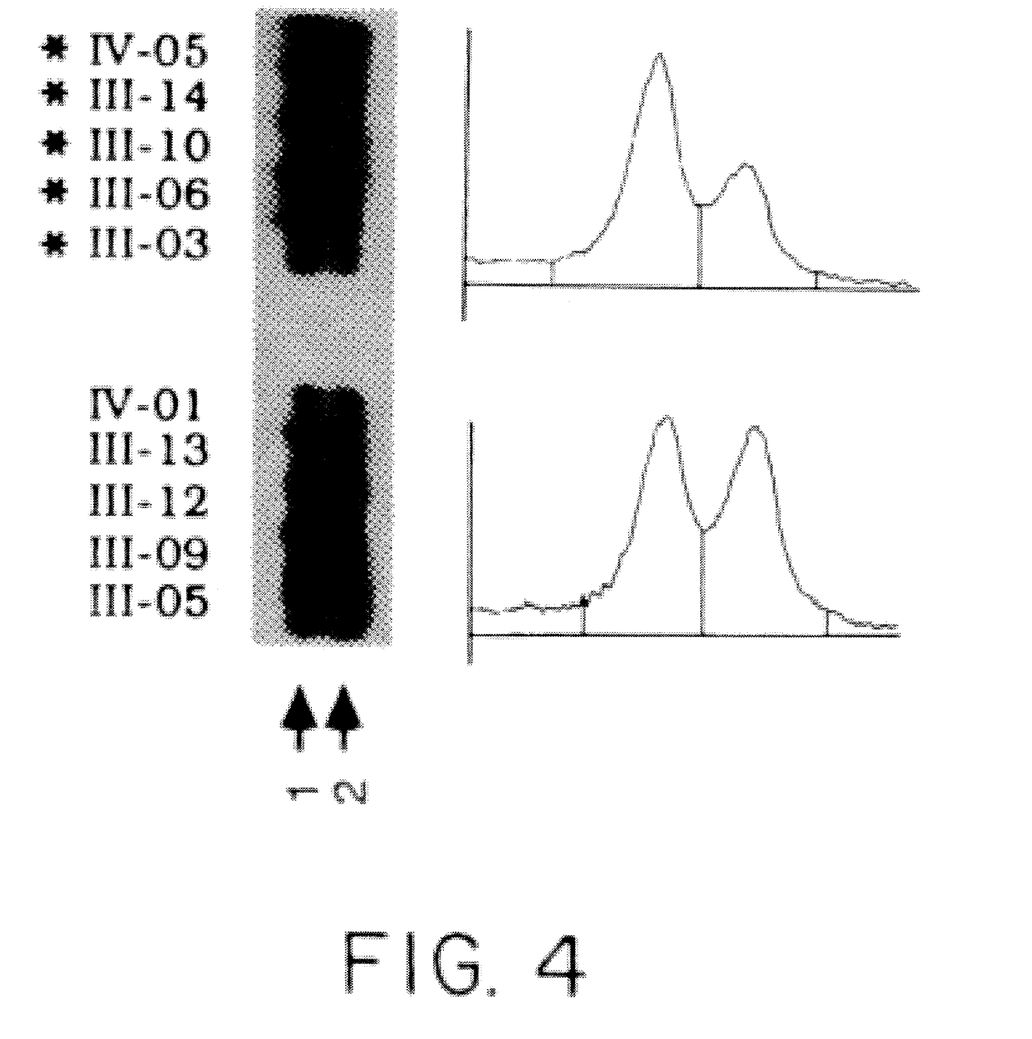
FIG. 4 is a photograph of a the autoradiogram of a gel representing the results of single strand conformational polymorphism of marker AldoX9 in 5 unaffected and 5 affected (,) subjects. Below the photograph is the densitometry results from the autoradiogram indicating the relative intensity of allele 1:allele 2 (arrowed bands) is 1:1 in unaffected subjects and 2:1 in affected subjects.

The products were quantitated by densitometry of a film exposed in the absence of intensifying screens. As shown in FIG. 4, the results indicate that all GRA individuals tested who are heterozygous for this 2-allele system show an approximate 2:1 ratio of alleles, indicating 3 copies of the 3' end of AldoS per diploid genome. All 145 unaffected heterozygotes show 1:1 ratio of alleles.

EXAMPLE 3

THE CHIMAERIC GENE DUPLICATION CARRIES ONLY THE 5' SEQUENCES SPECIFIC FOR 11-OHase AND NOT THE 5' SEQUENCES SPECIFIC FOR AldoS The procedure and reactants of Example 1 were used except a probe specific for the 5' end of AldoS was prepared by amplifying a specific 5' segment from genomic DNA using specific primers AldoX1 and AldoX2b, and purifying the fragment by agarose gel electrophoresis followed by GeneClean. This fragment was then reamplified and labeled in PCR using the same primers. This segment is 234 bp in length and extends from 330 to 554 bp upstream of exon 1 of AldoS.

Figure 5:
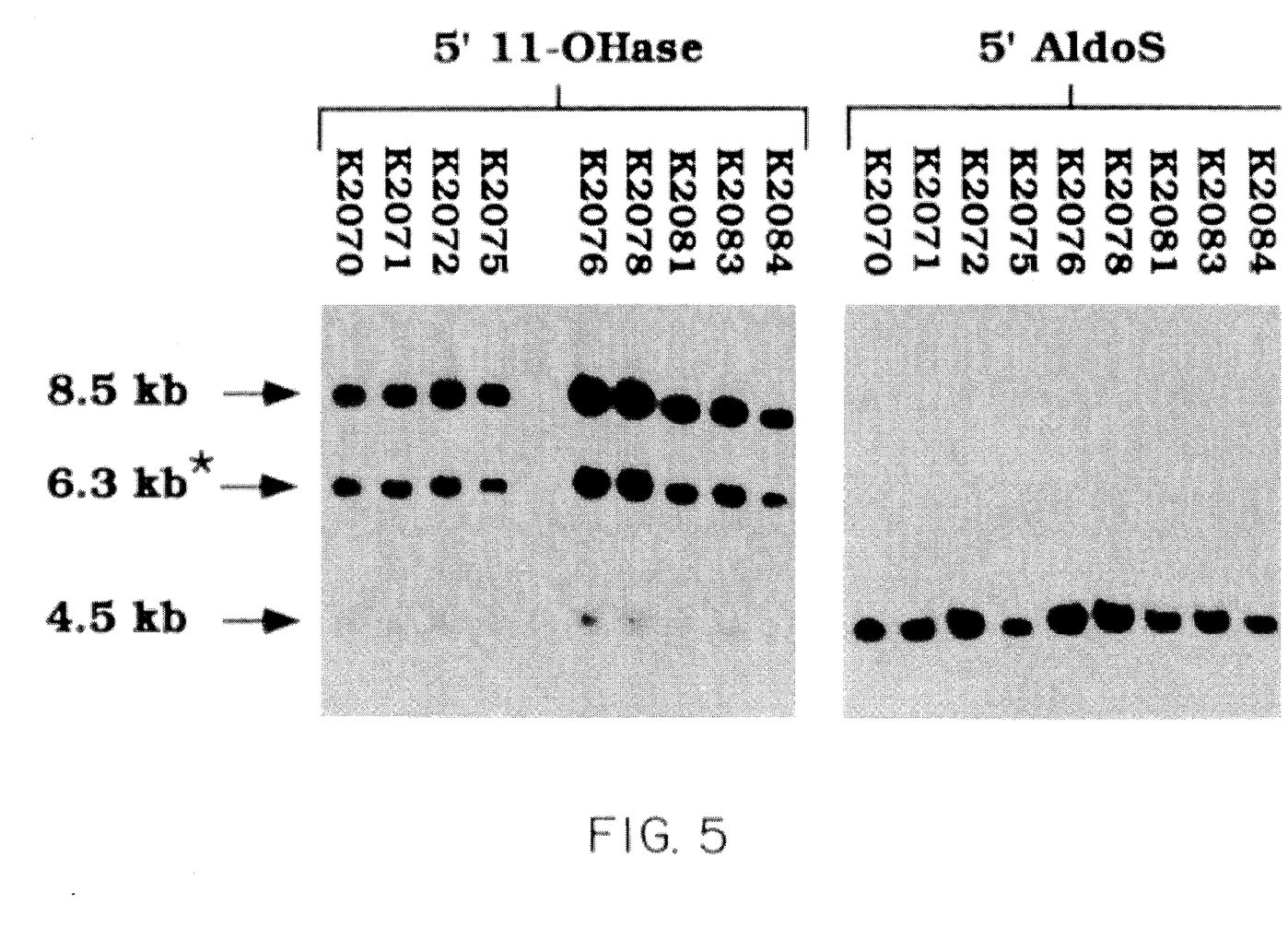
FIG. 5 is a photograph of a gel representing hybridization of fragments specific for the 5' end of either 11-OHase or AldoS to BamHI digested genomic DNA of patients with GRA.

Hybridization of fragments specific for the 5' end of either 11-OHase or AldoS to BamHI digested genomic DNA of individuals with GRA was performed using the Southern blot analysis as described in Example 1. Genomic DNA was digested with BamHI and Southern blotting and hybridization with the indicated probes performed. In each case, the 6.3 kb BamHI fragment derived from the chimaeric gene duplication hybridizes to the 5' end of 11-OHase but not to the 5' end of AldoS as demonstrated in FIG. 5.

These results provide further evidence that GRA patients harbor chimaeric gene duplications arising by unequal crossing over and fusing 5' 11-OHase sequences to more distal AldoS sequences.

EXAMPLE 4

IDENTIFICATION OF CROSS OVER BREAKPOINTS BY SEQUENCE ANALYSIS IN 11 GRA PATIENTS

The sequence differences among the 11-OHase, AldoS, and GRA genes were examined by DNA sequence analysis. The mutant gene from 11 GRA individuals was sequenced to examine the unequal crossing over model.

DNA Sequence Analysis of the haploid chimaeric gene duplications was performed on genomic DNA after amplification by PCR. In each case 10 ug of genomic DNA was digested with BamHI, fractionated on low-melting 0.7% agarose gels, and fragments of size 6.1–6.4 kb excised from the gel using λ-HindIII size standards as a guide. Additional fragments ranging from 4–9 kb were also excised. Gel slices were melted and a portion subjected to electrophoresis and Southern blotting, using exon 3-4 of 11-OHase as a probe to ensure that the 6.1–6.4 kb fraction contained the 6.3 kb chimaeric gene fragment free from contamination with either the 8.5 kb 11-OHase fragment or the 4.5 kb AldoS fragment.

Appropriate fragments were purified using GeneClean (Bio101), and segments of the chimaeric gene amplified with appropriate PCR primers. Primary amplifications were performed with primer sets. PCR was conducted for 30 cycles of 94° C. for 45 s, 60° C. for 45 s and 72° C. for 45 s in the presence of 100 μM dNTP's 1×PCR buffer (Cetus), and 25 u ml$^{-1}$ Taq polymerase. Products were purified by agarose gel electrophoresis followed by isolation using GeneClean. PCR was repeated using appropriate primers;. one primer coupled at the 5' end to either M13 universal or reverse primers. Products were purified and subjected to sequence analysis by dideoxy chain termination using fluorescently labeled universal or reverse primers and thermocycling (Applied Biosystems); products were analyzed using an ABI model 373 A DNA sequence apparatus.

11-OHase and AldoS genes were sequenced by the same approach using the 8.5 kb and 4.5 kb BamHI size fractions excised from agarose gel after electrophoresis. These genes were sequenced from 5 normal individuals and one GRA individual. The sequence differences identified between these two genes are similar to those described, although some of the variants previously described from sequence analysis of one cloned allele of each gene, particularly those in introns, were not detected in any samples.

Figure 6:
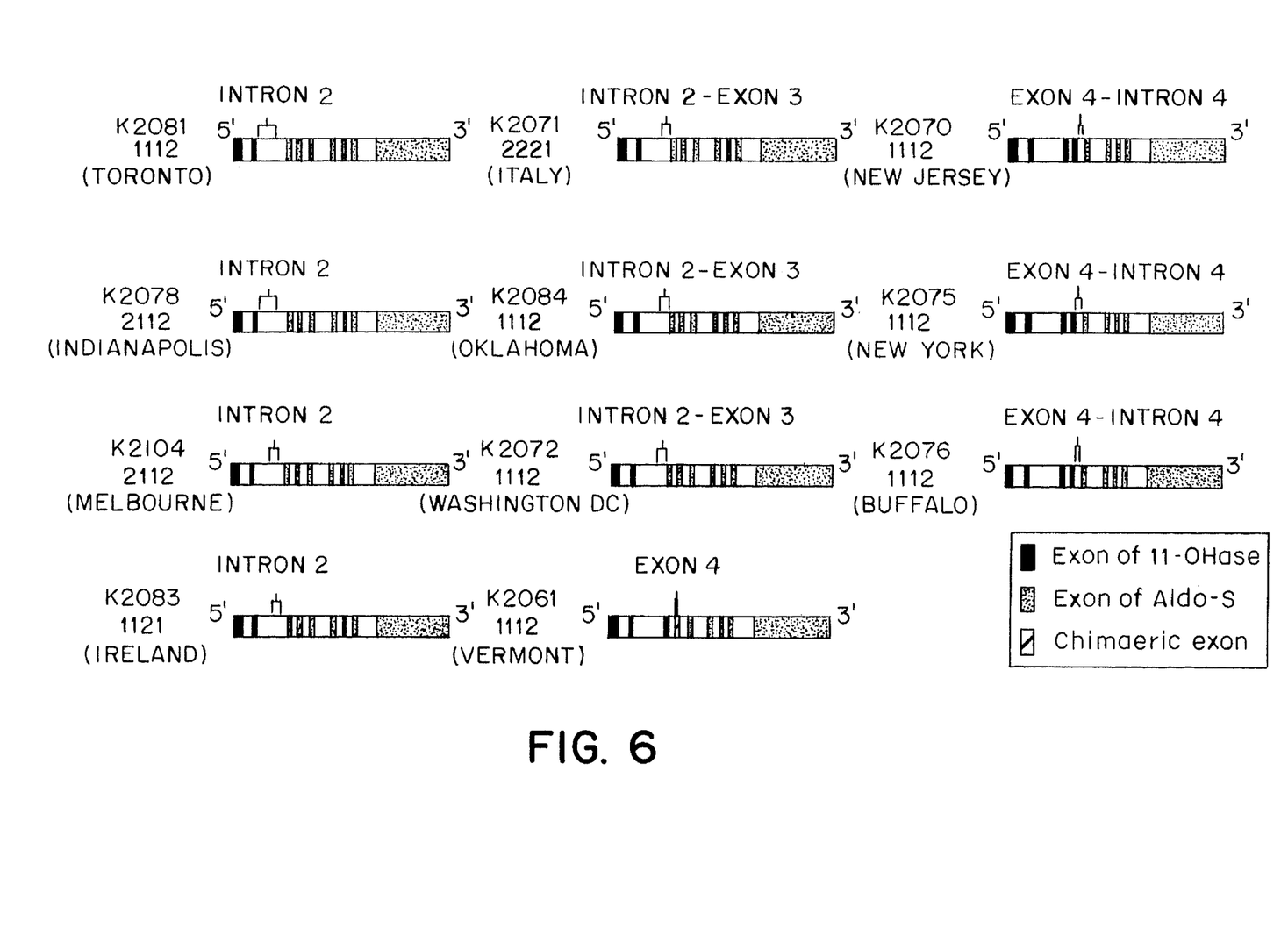
FIG. 6 is a schematic representation of inferred cross over sites in chimaeric genes from different GRA subjects.

In each case, exon 2 and a continuous segment from intron 2 to the end of exon 5 was sequenced and the sequences of the mutant gene compared to the normal AldoS and 11-OHase sequences. In all 11 GRA individuals, the mutant gene displays the predicted chimaeric structure, fusing 5' 11-OHase sequences to more distal AldoS sequences. The transition from bases specific for 11-OHase to bases specific for aldosterone synthetase is generally abrupt. Because of the extremely high homology of 11-OHase and AldoS, the site of crossing over can only be localized to within a few hundred base pairs in most cases. Three individual show crossover sites within the 300 bp segment between the last base distinguishing the two genes in exon 4 and the first base distinguishing these genes in intron 4. Other sites of crossover are within exon 4, at the junction of intron 2 and exon 3, and at least two different sites within intron 2. Three different chimaeric proteins are encoded among different pedigrees. The three different pedigrees with the most distal breakpoint encode proteins with exons 1–4 specific for 11-OHase and exons 5–9 specific for AldoS, indicating that there are no AldoS residues encoded in exon 1- 4 that are essential for the GRA phenotype and by inference, AldoS activity. See FIG. 6.

EXAMPLE 5

DETERMINATION OF THE DISTANCE BETWEEN 11-OHase AND AldoS GENES BY PULSE-FIELD GEL ELECTROPHORESIS The tight genetic linkage of 11-OHase and AldoS suggests that examination of the pulse field products of GRA individuals can be used to determine the distance between the two genes. Leukocytes were transformed, grown, and plugs were prepared. Electrophoresis and Southern blotting were performed as in Example 1 except ClaI was the restriction enzyme used for digestion of genomic DNA.

Lymphoblastoid cell lines were established by transformation of peripheral blood lymphocytes with Epstein-Barr virus. Resulting lymphoblastoid cell lines were cultured at 37° C., 5% $CO_2$ in RPMI 1640 medium (Cellgro/Mediatech) with 5% fetal bovine serum (Hyclone) and 50 U $ml^1$ gentamicin sulphate. Plugs for pulse-field gel analysis were prepared in 1% low melting agarose (Sigma) and digested with enzyme. Products were fractionated via transverse alternating field electrophoresis on a Geneline apparatus (Beckman Instruments). Samples were electrophoresed for 24 hours at 250 volts with pulse times of 30 seconds on 1% agarose gels in 0.5×TBE buffer at 10° C.

Figure 7:
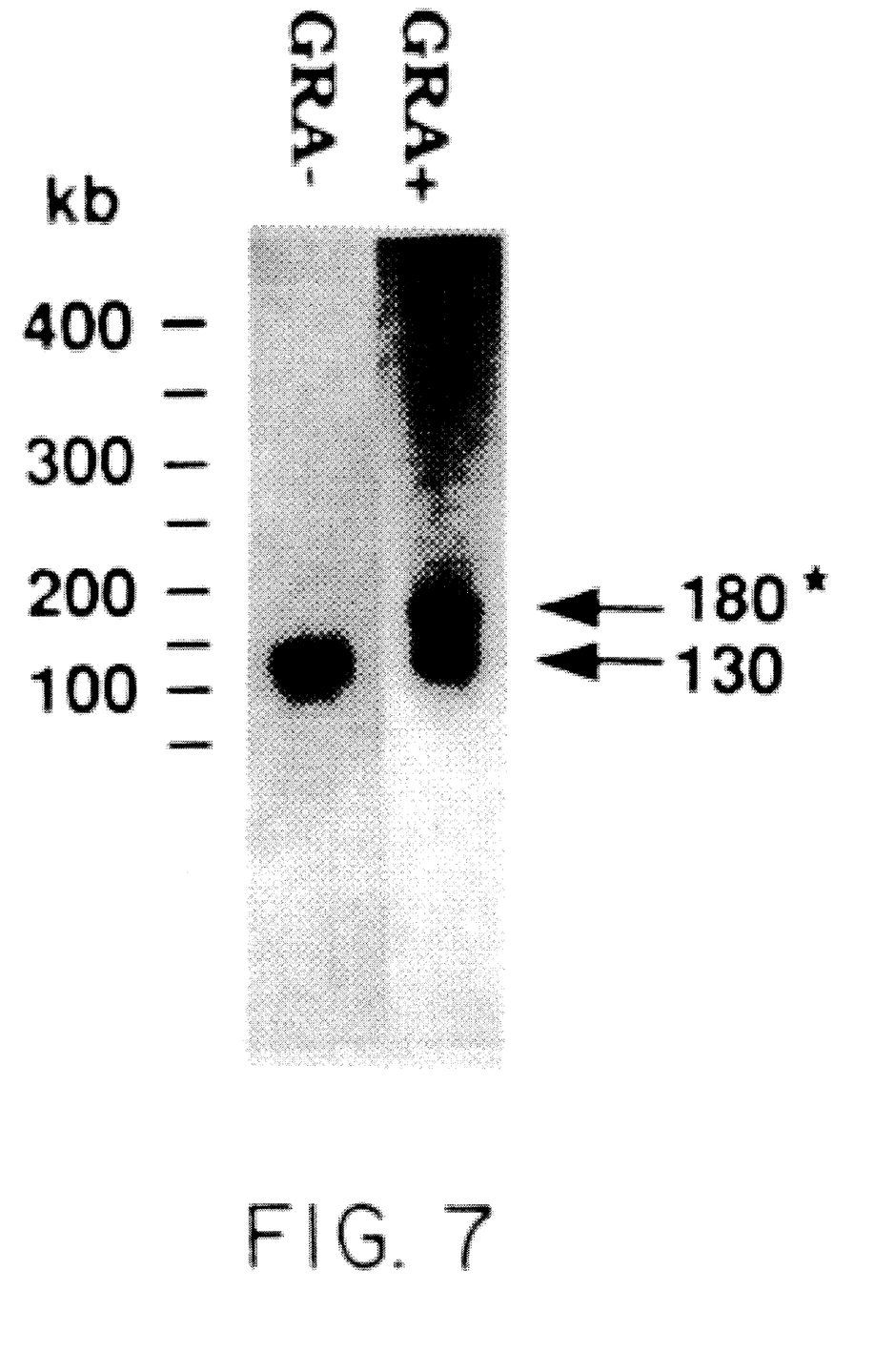
FIG. 7 is a photograph of the pulse-field gel analysis of GRA+ and GRA− subjects.

The rare-cutting restriction enzyme ClaI, cleaves the genomic DNA such that both the 11-OHase and AldoS genes on a normal chromosome are found on the same pulse field gel fragment. In such a case, after unequal crossing over, the allele carrying the resulting duplication will be larger than the normal allele. This increase in size, corresponds to the distance between the two genes on the normal chromosome plus the length of the duplicated gene. As the results indicated, in normal subjects, the 11-OHase and the AldoS genes are both present on a single fragment of 130 kb after digestion of genomic DNA with ClaI; in contrast, GRA patients show two hybridizing fragments of 130 kb and 180 kb in length. See FIG. 7. As the length of the duplicated gene is approximately 6 kb, the distance between 11-OHase and AldoS is approximately 45 kb.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of screening for glucocorticoid-remediable aldosteronism in a human by detecting the presence of a chimaeric gene duplication resulting from unequal crossing ever of the 11β-hydroxylase and aldosterone synthase genes, wherein presence of the chimaeric gene duplication is indicative of a human afflicted with glucocorticoid-remediable aldosteronism.

2. A method of detecting glucocorticoid-remediable aldosteronism in a human by:

a) cleaving a sample of the human's deoxyribonucleic acid (DNA) into DNA fragments;

b) separating the DNA fragments of (a);

c) exposing the separated DNA fragments of (b) to labeled DNA sequences complementary to the sequences of particular DNA fragments of (b), where one of the labeled-complementary DNA sequences is complementary to the sequence of a chimaeric gene duplication resulting from the unequal crossing over of the 11β-hydroxylase and aldosterone synthase genes present in the genomic DNA of affected humans and absent in the genomic DNA of unaffected humans, under conditions appropriate for hybridization to occur;

wherein hybridization of one of the DNA fragments in (b) to a labeled DNA sequence in (c) which is complementary to the chimaeric gene duplication is indicative of a human afflicted with glucocorticoid-remediable aldosteronism.

3. A method of detecting glucocorticoid-remediable aldosteronism in a human by:

a) obtaining a sample of the human's deoxyribonucleic acid (DNA);

b) cleaving a sample of the human's DNA of (a) into DNA fragments using restriction enzymes;

c) separating the DNA fragments of (b) using gel electrophoresis;

d) exposing the separated DNA fragments of (c) to radiolabeled DNA sequences complementary to the sequences of particular DNA fragments of (c), where one of the radiolabeled complementary DNA sequences is complementary to the sequence of a chimaeric gene duplication resulting from the unequal crossing over of the 11β-hydroxylase and aldosterone synthase genes present in the genomic DNA of affected human and absent in the genomic DNA of unaffected humans, under conditions appropriate for hybridization to occur;

wherein hybridization of one of the DNA fragments in (c) to a radiolabeled DNA sequence of (d) which is complementary to the sequence of the chimaeric gene duplication is indicative of a human afflicted with glucocorticoid-remediable aldosteronism.

4. A method of claim 3 wherein the restriction enzymes of (b) are from the group consisting of: BamHI, EcoRI, HindIII, ClaI and PvuII.

5. A method of detecting glucocorticoid-remediable aldosteronism in a human by:

a) cleaving a sample of the human's deoxyribonucleic acid (DNA) into DNA fragments using BamHI;

b) separating the DNA fragments of (a) using gel electrophoresis;

c) exposing the separated DNA fragments of (b) to radiolabeled DNA sequences complementary to the sequences of particular DNA fragments of (b), where one of the radiolabeled cumplementary DNA sequences is complementary to a 6.3 kilobase DNA fragment present in the genomic DNA of affected humans and absent in the genomic DNA of unaffected humans, under conditions appropriate for hybridization to occur;

wherein hybridization of one of the DNA fragments in (b) to the radiolabeled DNA with the sequence complementary to the 6.3 kilobase DNA fragment in (c) is indicative of a human afflicted with glucocorticoid-remediable aldosteronism.

6. A method of detecting glucocorticoid-remediable aldosteronism in a human by:

a) cleaving a sample of the human's deoxyribonucleic acid (DNA) into DNA fragments using EcoRI;

b) separating the DNA fragments of (a) using gel electrophoresis;

c) exposing the separated DNA fragments of (b) to radiolabeled DNA sequences complementary to the sequences of particular DNA fragments of (b), where one of the radiolabeled complementary DNA sequences is complementary to a 22 kilobase DNA fragment present in the genomic DNA of affected humans and absent in the genomic DNA of unaffected humans, under conditions appropriate for hybridization to occur;

wherein hybridization of one of the DNA fragments in (b) to the radiolabeled DNA with the sequence complementary to the 22 kilobase DNA fragment in (c) is indicative of a human afflicted with glucocorticoid-remediable aldosteronism.

7. A method of screening for glucocorticoid-remediable aldosteronism in a human by detecting chimaeric gene duplications in the human's genomic DNA using restriction enzymes to fragment a sample of the human's DNA which will yield a characteristic DNA sequence of a chimaeric gene duplication which is detected upon hybridization with a labeled DNA sequence complementary to the sequence of the chimaeric gene duplication associated with glucocorticoid-remediable aldosteronism.

8. A method of screening for glucocorticoid-remediable aldosteronism in a large number of samples using polymerase chain reaction with one primer specific for the 11-hydroxylase gene sequences and another specific for the aldosterone synthase gene sequences whereby only chimaeric genes can yield products of pro-determined length and detecting the presence of a chimaeric gene duplication resulting from unequal crossing over of the 11$\beta$-hydroxylase and aldosterone synthase genes, wherein presence of the chimaeric gene duplication or its product is indicative of a human afflicted with glucocorticoid-remediable aldosteronism.

* * * * *